United States Patent [19]
Kandori et al.

[11] Patent Number: 5,429,721
[45] Date of Patent: Jul. 4, 1995

[54] PROCESS FOR PREPARING DIACETOXYBUTENE

[75] Inventors: Hiroaki Kandori; Nobuyuki Murai, both of Yotsukaichi, Japan

[73] Assignee: Mitsubishi Chemical Corporation, Tokyo, Japan

[21] Appl. No.: 245,663

[22] Filed: May 18, 1994

[30] Foreign Application Priority Data

May 19, 1993 [JP] Japan .................................. 5-117254

[51] Int. Cl.$^6$ .......................... B01D 3/10; C07C 69/02
[52] U.S. Cl. ........................................ 203/72; 203/73; 203/78; 203/80; 560/244
[58] Field of Search .................. 203/72, 73, 78, 80; 560/244; 159/49

[56] References Cited

U.S. PATENT DOCUMENTS

| | | | |
|---|---|---|---|
| 4,057,472 | 11/1977 | Toriya et al. | 203/80 |
| 4,150,239 | 4/1979 | Tanabe et al. | 560/244 |
| 4,225,729 | 9/1980 | Toriya et al. | 560/244 |
| 4,228,301 | 10/1980 | Yoshida et al. | 203/42 |
| 4,236,024 | 11/1980 | Matsuda et al. | 560/244 |
| 5,177,254 | 1/1993 | Haji et al. | 560/244 |

FOREIGN PATENT DOCUMENTS 2627001 2/1977 Germany .
3224509 1/1984 Germany .

*Primary Examiner*—Virginia Manoharan
*Attorney, Agent, or Firm*—Oblon, Spivak, McClelland, Maier, & Neustadt

[57] ABSTRACT

A process for preparing diacetoxybutene, including:

reacting butadiene, acetic acid and oxygen in the presence of a palladium-based catalyst;

feeding continuously the resulting reaction product into a first distillation tower;

feeding continuously a withdrawn bottoms withdrawn from the first distillation tower into a second distillation tower;

withdrawing bottoms containing high boiling point materials from the bottom of the second distillation tower, so that the content of the high boiling point materials in the bottoms of the second distillation tower is not more than 20 wt %;

feeding continuously the withdrawn bottoms into a thin-film evaporator whose internal pressure is kept lower than the bottom pressure of the second distillation tower to carry out evaporation treatment; and recycling the evaporated materials mainly containing diacetoxybutene into the second distillation tower.

11 Claims, 1 Drawing Sheet

PROCESS FOR PREPARING DIACETOXYBUTENE

BACKGROUND THE INVENTION

The present invention relates to a process for preparing diacetoxybutene. Diacetoxybutene is an important raw material for the production of 1,4-butanediol and tetrahydrofuran which are utilized as a solvent or synthetic resin material.

Diacetoxybutene is usually produced by reacting butadiene, acetic acid and oxygen in the presence of a palladium catalyst. It is necessary to separate diacetoxybutene from the acetoxylation reaction product, but some problems are involved in this process. Since both of the unreacted materials and diacetoxybutene contained in the reaction product have unsaturated groups (unsaturated radicals), there can be generated polymeric substances as a by-product depending on the treatment involved, and such generation of the polymeric substances as a by-product may become a cause of decrease of yield or operational impediment.

Japanese Patent Application Laid-Open (KOKAI) No. 50121210 (corresponding to U.S. Pat. No. 4,057,472) teaches that diacetoxybutene can exist in relatively stable when distillation for separating diacetoxybutene from the said reaction product is carried out by controlling the pressure within the distillation tower while maintaining the temperature of the bottom of the distillation tower at lower than 190° C., and as a result, the above-mentioned problems have been solved.

However, for separating and recovering diacetoxybutene from the reaction product in a high yield, it is essentially required to prolong the residence time of the reaction products in the distillation tower. Therefore, even if the temperature of the bottom of the distillation tower is kept low, for example, not higher than 190° C., it is hardly possible to perfectly prevent occurrence of polymerization and decomposition, and there can arise the problems such as mixing of the decomposed substances in the distillate diacetoxybutene from the distillation tower and blockage of an outlet for withdrawing the bottoms due to deposition of the polymeric substances to the heater at the bottom of the distillation tower. Thus, in the conventional processes, in order to avoid the abovementioned problems it has been inevitable that bottoms of the distillation tower containing diacetoxybutenes as well as high boiling point materials be discarded.

As a result of the present inventors' strenuous studies for satisfying the demands, it has been found that in the process for preparing diacetoxybutene comprising reacting butadiene, acetic acid and oxygen in the presence of a palladium-based catalyst, distilling the reaction product in a first distillation tower to distill off acetic acid and water, and further distilling the residual materials in a second distillation tower, by withdrawing the obtained bottoms from the second distillation tower in a situation where the content of high boiling point materials in the bottoms of the second distillation tower is not raised above 20%, subjecting the withdrawn bottoms to evaporation treatment in a thin-film evaporator, and returning the evaporated materials containing diacetoxybutene to the second distillation tower, it is possible to obtain diacetoxybutene with higher purity in a higher yield. The present invention has been attained on the basis of this finding.

SUMMARY OF THE INVENTION

It is an object of the present invention to provide a diacetoxybutene preparation process which is capable of producing high-purity diacetoxybutene in a high yield with trouble-free operation.

To accomplish the aims, in an aspect of the present invention, there is provided a process for preparing diacetoxybutene, which comprises:

reacting butadiene, acetic acid and oxygen in the presence of a palladium-based catalyst;

feeding continuously the resulting reaction product into a first distillation tower to distill off water and acetic acid from the top of the first distillation tower;

withdrawing bottoms which contain mainly diacetoxybutene, from the bottom of the first distillation tower;

feeding continuously the bottoms withdrawn from the first distillation tower into a second distillation tower for distilling out and recovering diacetoxybutene from the top of the second distillation tower;

withdrawing bottoms containing high boiling point materials from the bottom of the second distillation tower, so that the content of the high boiling point materials in the bottoms of the second distillation tower is not more than 20 wt %;

feeding continuously the withdrawn bottoms into a thin-film evaporator whose internal pressure is kept lower than the bottom pressure of the second distillation tower to carry out evaporation treatment; and recycling the evaporated materials mainly containing diacetoxybutene into the second distillation tower.

DETAILED DESCRIPTION OF THE INVENTION

Figure 1:
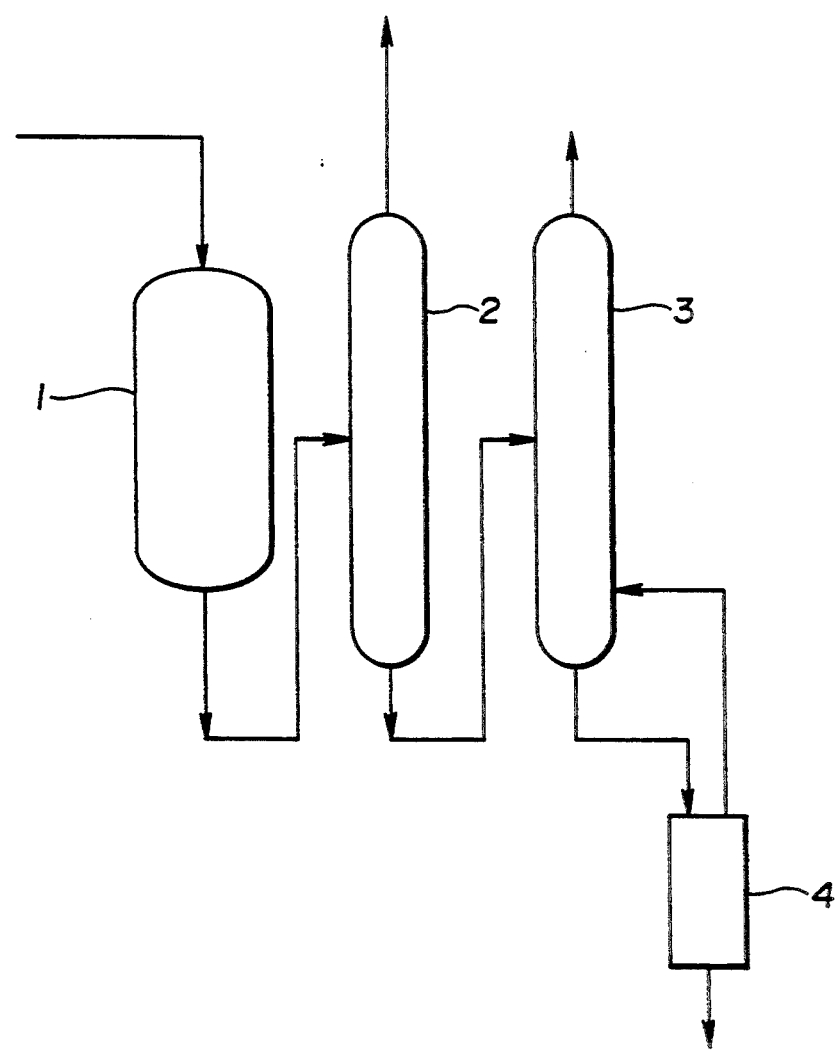
FIG. 1 illustrates the process according to the present invention.

The reaction product used in the present invention is an acetoxylation reaction product obtained by reacting butadiene, acetic acid and oxygen in the presence of a palladium-based catalyst. This acetoxylation reaction is not subjected to specific restrictions but can be carried out in accordance with the known procedure which is described in U.S. Pat. Nos. 4,150,239 and 5,177,254. In such acetoxylation reaction, the amounts of the reactants used are, for example, 3 to 5 moles of acetic acid and 7 to 15 moles of oxygen based on one mole of butadiene.

As the palladium-based catalyst, there can be used palladium metal or a salt thereof singly or in combination with a cocatalyst of a metal such as bismuth, selenium, antimony, tellurium, copper or the like or a salt thereof. The catalyst supported on a carrier such as silica, alumina, activated carbon or the like is preferably used. As for the amounts of the catalyst metals in the supported catalyst, usually the amount of palladium metal is selected from the range of 0.1 to 20 wt % and the amount of other cocatalyst metal from the range of 0.01 to 30 wt %.

The acetoxylation reaction can be carried out according to any suitable system such as fixed bed system, fluidized bed system, suspending catalyst system, etc., but usually fixed bed system is preferred. The reaction is usually carried out at a temperature in the range of 40 to 180° C., preferably 60 to 150° C., under normal pressure or above.

The thus obtained acetoxylation reaction product contains unreacted butadiene and other undesirable substances, so that the reaction product is preferably subjected to distillation described below after undergoing a degassing treatment.

In the degassed reaction product are contained, beside diacetoxybutene, monodiacetoxybutene, triacetoxybutene, water produced by the acetoxylation reaction, acetic acid, high boiling point materials and so on. The composition of this reaction product is usually 10 to 25 wt % of diacetoxybutene, 90 to 60 wt % of acetic acid, 1 to 5 wt % of water and 0.5 to 3 wt % of the high boiling point materials.

In case the reaction is carried out according to the fluidized bed or suspending catalyst system, it is necessary to separate a solid catalyst from the reaction product before recovering diacetoxybutene.

In the present invention, the reaction product is fed into a first distillation tower for distilling off substantially all (not less than 99 wt %) of water and acetic acid, and the bottoms (materials remaining in the bottom) of the first distillation tower is fed into a second distillation tower. As for the operation conditions of the respective distillation towers, the temperature of the bottom of the distillation tower is maintained usually at not more than 190° C., preferably 120 to 180° C., and the top pressure of the distillation towers is usually set at 30 to 300 mmHg for the first tower and 2 to 100 mmHg for the second tower. When the temperature in the bottom of the distillation towers exceeds 190° C., decomposition and polymerization of acetoxybutene is accelerated excessively. The pressures of the respective towers are preferably so controlled that the pressure of the first distillation tower is lower than the pressure of the second distillation tower.

The residence time of the bottoms of the respective distillation towers varies depending on the design of the towers and distilling conditions, but usually it is 10 to 60 minutes in the case of the first tower and 1 to 10 hours in the case of the second tower.

Each distillation tower may be constituted by two or more units of tower. For instance, the first distillation tower may composed of a normal pressure column and a reduced pressure column, so that acetic acid and water are roughly distilled off by the normal pressure column and then they are substantially distilled off by the reduced pressure column.

If necessary, between the first distillation tower and the second distillation tower, or after the second distillation tower, another tower for separating isomers of diacetoxybutene may be provided.

In the second distillation tower, the materials (bottoms) withdrawn from the bottom of the first distillation tower is distilled and separated into diacetoxybutene and high boiling point materials, and the objective diacetoxybutene is recovered. In the present invention, diacetoxybutene is distilled out from the top of the second distillation tower while the content of the high boiling point materials in the bottoms of the second distillation tower is maintained at not more than 20 wt %, preferably not more than 15 wt %.

When the concentration of the high boiling point materials in the bottoms of the second distillation tower exceeds 20 wt %, the residence time of high boiling point materials at the bottom of the second distillation tower is accordingly prolonged, thereby elevating a bottom temperature of the second distillation tower and encouraging polymerization and decomposition of diacetoxybutenes, etc. Consequently, the decomposed materials may get mixed in the distillate and the viscosity of the bottoms may be increased to make it difficult to withdraw the bottoms and to even cause a hindrance to the normal distilling operation.

The distilling-out amount of diacetoxybutene from the second distillation tower is not so high, as the bottoms is withdrawn from the second distillation tower so that the concentration of high boiling point materials in the bottoms does not exceed the above-mentioned range. Namely, the content of diacetoxybutene contained in the bottoms withdrawn from the bottom of the second distillation tower is usually 3 to 40 wt %, preferably 6 to 20 wt % based on the amount of diacetoxybutene contained in the materials withdrawn from the bottom of the first distillation tower. The "high boiling point materials" in the present invention mean substances having a higher boiling point than diacetoxybutene under an ordinary pressure, particularly, substances which do not boil at a temperature of not more than 250° C. under an ordinary pressure. The high boiling point materials are composed of substances whose boiling point is usually not less than 250° C. and/or which are thermally decomposed before vaporized. Such high boiling point materials are not specified in their structure, but most of them are supposed to be the polymers of butadiene and/or diacetoxybutene.

A considerable amount of diacetoxybutene is contained in the bottoms of the second distillation tower, so that in the present invention the said bottoms is further treated in a thin-film evaporator to separate the residual diacetoxybutene from the bottoms, and substantially whole of diacetoxybutene which is contained in bottoms is recycled into the second distillation tower, while the high boiling point materials are purged. The concentration of diacetoxybutene in the evaporated materials can be as high as 80% or above, but as they contain the undesirable byproducts such as triacetoxybutene, it is necessary to be recycled into the second distillation tower.

In operation of the thin-film evaporator, its internal pressure is so controlled that the pressure thereof is lower than the bottom pressure of the second distillation tower. This makes it possible to evaporate and recover the useful substance: diacetoxybutene in the bottoms withdrawn from the second distillation tower while separating the high boiling point materials as non-evaporated matter. The pressure of the said evaporator is usually set within the range of 1 to 50 mmHg. The evaporating temperature is preferably set at not more than 190° C. as well as the bottom temperature of the first and second distillation towers. The average residence time of the bottoms to be evaporated is usually 0.5 to 10 minutes, preferably 1 to 5 minutes, which is very short as compared with the residence time of the distillation towers.

The thin-film evaporator used in the present invention need not be of a specific structure. It may be of the same structure as the commercially available evaporators, and there can be used various types of thin-film evaporators, such as vertical thin-film evaporator, plate-type downcast thin-film evaporator and tube-type downcast thin-film evaporator.

In accordance with the present invention, diacetoxybutene can be distilled and recovered from the said reaction product by an industrially stable operation without causing blockage of the distillation towers, i.e. the blockage of the outlet for withdrawing the bottoms in the distillation towers, and other troubles. Also, the recovery rate of diacetoxybutene and the quality of recovered diacetoxybutene are high. It is notable that the purity of diacetoxybutene recovered from the top of the second distillation tower used in the present invention is higher than 80 wt %, and quite remarkably the content of 1,1,4-triacetoxybutene, which is an undesirable by-product, is less than 1 wt %

An embodiment of the present invention is illustrated in FIG. 1. Acetoxytation reaction is carried out in reactor 1, and after the reaction product has been degassed by a gas/liquid separator (not shown), the liquid phase (reaction product) is fed into first distillation tower 2 where water, acetic acid and other low-boiling substances are distilled off and the bottoms withdrawn from the first distillation tower is fed into second distillation tower 3. Diacetoxybutene is distilled out from the top of the second distillation tower 3. Also, a part of the bottoms is withdrawn, and the evaporated materials from thin-film evaporator 4 is recycled into second distillation tower 3.

In the process of the present invention, distillation of diacetoxybutene is carried out under the relatively mild conditions with the distilling-out rate of diacetoxybutene being limited and the withdrawing rate of the bottoms from the second distillation tower being increased. The withdrawn bottoms is fed into a thin-film evaporator. The residence time of the bottoms in the thin-film evaporator is very short, and the high boiling point materials can be removed efficiently. Further, the most portion of diacetoxybutene in the bottoms can be recovered. It is possible with this process to recover diacetoxybutene with high purity in a high yield. The present invention is therefore of high industrial utility.

The present invention is further illustrated below with reference to the examples.

In the following Examples, all "parts" are by weight unless otherwise noted.

Example 1

Diacetoxybutene was prepared according to the process flow shown in FIG. 1. Butadiene, acetic acid and oxygen were reacted in the presence of a palladium-based catalyst composed of activated carbon with 2 wt % of palladium and 0.1 wt % of tellurium supported thereon at a temperature of 100° C. under a pressure of 90 kg/cm$^2$ to obtain a reaction product containing 15.4 wt % of diacetoxybutene (1.4-form being 14.0 wt %) and 1.1 wt % of high boiling point materials. The reaction product was fed into the first distillation tower at a rate of 3,600 parts/hr and distilled under the following conditions:

Bottom temperature: 144° C.
Top pressure: 90 mmHg
Average residence time: 0.5 hr (bottom)
Reflux ratio: 0.07
Real number of plates: 10

In the first distillation tower, the most portion of water and acetic acid were distilled off at a rate of 2,940 parts/hr, while the bottoms containing 82.0 wt % of diacetoxybutene (1,4-form being 74.1 wt %) and 6.2 wt % of high boiling point materials was withdrawn at a rate of 660 parts/hr.

The bottoms withdrawn from the said first distillation tower was fed into the second distillation tower at a rate of 660 parts/hr. Also evaporated materials from a thin-film evaporator described later was returned into the second distillation tower at a rate of 40 parts/hr, and the mixture of the bottoms and evaporated materials was distilled in the second distillation tower under the following conditions:

Bottom temperature: 148° C.
Top pressure: 20 mmHg
Average residence time: 9 hr (bottom)
Reflux ratio: 0.41
Real number of plates: 17

In the second distillation tower, diacetoxybutene with a purity of 84.4% (1,4-form being 76.3 wt %) was distilled out at a rate of 634 parts/hr. (Approximately 93% of diacetoxybutene fed to the second distillation tower was distilled out). Also, the bottoms (containing 59.5 wt % of 1,4-diacetoxybutene and 20.0 wt % of high boiling point materials) was withdrawn at a rate of 66 parts/hr.

The said bottoms was fed into the thin-film evaporator and subjected to thin-film evaporation under the following conditions:

Internal pressure: 15 mmHg
Evaporating temperature: 175° C.
Average residence time: 1 min (bottom)

There was consequently obtained the evaporated materials (86.0 wt % of diacetoxybutene (1,4-form being 85.0 wt %)) at a rate of 40 parts/hr, and this was recycled to the second distillation tower.

The above operation was run continuously for about a month, and there was steadily obtained 1,4-diacetoxybutene with a constant purity during the run.

Comparative Example 1

The same preparation of diacetoxybutene as in Example 1 except that the continuous distillation in the second distillation tower was carried out under the following conditions:

Bottom temperature: 151° C.
Top pressure: 25 mmHg
Reflux ratio: 0.4
Real number of plates: 12

No thin-film evaporator was used, and the concentration of the high boiling point materials in the bottoms was increased for elevating the distillation yield of diacetoxybutene. However, the viscosity of the bottoms rose sharply when the concentration of the high boiling point materials exceeded about 20 wt %, and it was hard to withdraw the bottoms when the said concentration elevated to 40 wt %.

What is claimed is:

1. A process for preparing diacetoxybutene, which comprises:

reacting butadiene, acetic acid and oxygen in the presence of a palladium-based catalyst;

feeding continuously the resulting reaction product into a first distillation tower to distill off by-product water and unreacted acetic acid from the top of the first distillation tower;

withdrawing bottoms which contain mainly diacetoxybutene, from the bottom of the first distillation tower;

feeding continuously the bottoms withdrawn from the first distillation tower into a second distillation tower for distilling out and recovering diacetoxybutene from the top of the second distillation tower;

withdrawing bottoms containing high boiling point materials from the bottom of the second distillation tower, so that the content of the high boiling point materials in the bottoms of the second distillation tower is not more than 20 wt %;

feeding continuously the withdrawn bottoms into a thin-film evaporator whose internal pressure is kept lower than the bottom pressure of the second distillation tower to carry out evaporation treatment; and recycling the evaporated materials mainly containing diacetoxybutene into the second distillation tower.

2. The process according to claim 1, wherein the amount of diacetoxybutene contained in the bottoms withdrawn from the bottom of the second distillation tower is 3 to 40 wt % based on the amount of diacetoxybutene in the bottoms withdrawing from the bottom of the first distillation tower.

3. The process according to claim 1, wherein the bottom temperatures of the first and second distillation towers and the evaporation temperature of the thin-film evaporator are controlled to be not more than 190° C..

4. The process according to claim 1, wherein the composition of the reaction product fed to the first distillation tower is 10 to 25 wt % of diacetoxybutene, 60 to 90 wt % of acetic acid, 1 to 5 minutes wt % of water and 0.5 to 3 wt % of the high boiling point materials.

5. The process according to claim 1, wherein the purity of diacetoxybutene recovered from the top of the second distillation tower is not less than 80 wt %, and the content of the by-product 1,1,4-triacetoxybutene is less than 1 wt %.

6. The process according to claim 3, wherein the bottom temperature of the first and second distillation towers is 120 to 180° C.

7. The process according to claim 1, wherein the top pressure of the first distillation tower is 30 to 300 mmHg, and the top pressure of the second distillation tower is 2 to 100 mmHg and lower than that of the first distillation tower.

8. The process according to claim 1, wherein the internal pressure of the thin-film evaporator is 1 to 50 mmHg.

9. The process according to claim 1, wherein the average residence time of the reaction product to be treated in the first distillation tower is 10 to 60 minutes, and the average residence time of the materials in the second distillation tower is 1 to 10 hours.

10. The process according to claim 1, wherein the average residence time of the bottoms to be treated in the thin-film evaporator is 1 to 5 minutes.

11. The process according to claim 1, wherein the content of the high boiling point materials in the bottoms withdrawn from the second distillation tower is controlled to be nor more than 15 wt %.

* * * * *

UNITED STATES PATENT AND TRADEMARK OFFICE
CERTIFICATE OF CORRECTION

PATENT NO. : 5,429,721
DATED : JULY 4, 1995
INVENTOR(S) : HIROAKI KANDORI ET AL

It is certified that error appears in the above-indentified patent and that said Letters Patent is hereby corrected as shown below:

Column 7, line 23, please delete "minutes".

Signed and Sealed this

Twenty-eighth Day of May, 1996

Attest:

BRUCE LEHMAN

*Attesting Officer*   *Commissioner of Patents and Trademarks*